(12) United States Patent
Huang et al.

(10) Patent No.: US 8,198,461 B2
(45) Date of Patent: Jun. 12, 2012

(54) PROCESS FOR THE PREPARATION OF 3-CYANO-1,2,4-TRIAZOLES

(75) Inventors: Der-Shing Huang, Folsom, CA (US); Benjamin Mendoza, Sacramento, CA (US); Aslam A. Malik, Cameron Park, CA (US)

(73) Assignee: AMPAC Fine Chemicals LLC., Rancho Cordova, CA (US)

( * ) Notice: Subject to any disclaimer, the term of this patent is extended or adjusted under 35 U.S.C. 154(b) by 228 days.

(21) Appl. No.: 12/437,711

(22) Filed: May 8, 2009

(65) Prior Publication Data

US 2009/0292122 A1    Nov. 26, 2009

Related U.S. Application Data

(60) Provisional application No. 61/051,407, filed on May 8, 2008.

(51) Int. Cl.
*C07D 249/10* (2006.01)

(52) U.S. Cl. .................................................. 548/266.8
(58) Field of Classification Search ................ 548/266.8
See application file for complete search history.

(56) References Cited

U.S. PATENT DOCUMENTS

| 3,691,178 A | 9/1972 | Baldwin et al. |
| 4,619,991 A | 10/1986 | Matzinger |
| 5,306,694 A | 4/1994 | Phillips et al. |
| 2008/0015233 A1 | 1/2008 | Barrow et al. |

FOREIGN PATENT DOCUMENTS

CN        1760186     *   4/2006

* cited by examiner

*Primary Examiner* — James O Wilson
*Assistant Examiner* — Douglas M Willis
(74) *Attorney, Agent, or Firm* — Kilpatrick Townsend & Stockton LLP.

(57) ABSTRACT

The present invention provides compounds and methods that can be used to convert 1,2,4-triazole-3-carboxamides to the corresponding 3-cyano-1,2,4-triazoles reliably in one step, with high yields and without the need for elaborate purification.

21 Claims, No Drawings

PROCESS FOR THE PREPARATION OF 3-CYANO-1,2,4-TRIAZOLES

CROSS REFERENCES TO RELATED APPLICATIONS

This application is claims the benefit of U.S. Provisional Patent Application No. 61/051,407, filed May 8, 2008; the entire disclosure of which are incorporated herein by reference.

BACKGROUND OF THE INVENTION

Three general routes have been developed for the synthesis of cyano-substituted-nitrogen containing heteroaryl compounds. These are illustrated below in Schemes 1a, b and c.
Scheme 1. Synthesis of Cyano-Substituted Nitrogen Containing Heteroaryl Compounds.
a. Cyclization of Acyclic Precursors

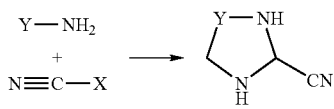

b. Synthesis by Functional Group Introduction

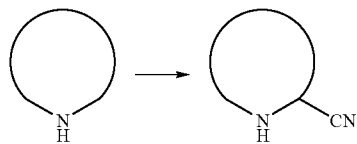

c. Synthesis by Functional Group Interchange

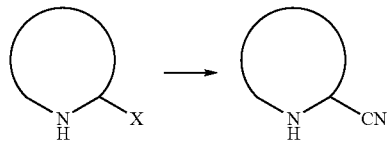

Cyano-substituted-nitrogen-containing heteroaryl compounds are valuable chemical intermediates for the preparation of a number of drugs. For example, 3-cyano-1H-1,2,4-triazole (3-CNT) is a key intermediate in the preparation of Ribavirin, which is used in treating Hepatitis C (see, U.S. Pat. Nos. 3,927,216 and 4,138,547). 4-Cyanoimidazole is key intermediate in the preparation of both pharmaceuticals and agrochemicals as well as crosslinking agents for epoxy resins (see, Less et al., Inorg. Chem. 2004, Japanese Patent No. 06073018). 2-Cyanopyrazine is key intermediate in the preparation of anti-microbial agents (see, Johnston et al., U.S. Pat. Nos. 4,442,095, 4,442,096 and 4,442,097; Beutel et al., U.S. Pat. No. 3,555,021); anti-inflammatory agents (see, U.S. Pat. No. 4,778,890; Opletalova et al., Coll. Czech. Chem. Comm. 61(7): 1093-11-01 (1996); and anti-tuberculosis drugs (see Indian Patent Nos. 177,142; 182,184; 182,185 and 185,265; Foks and Sawlewicz Acta Polonia Pharmaceutica 25(2): 137-42 (1968)). As discussed in more detail below, various synthetic routes for these useful intermediates have been reported in literature. Unfortunately, these molecules are often difficult to be produced on a large scale by known synthetic methods.

Cyanotriazoles

Few routes have been published in the literature for the synthesis of 3-CNT and these have not been commercialized. Using the first method, 3-CNT is manufactured beginning with cyanogen and anhydrous hydrazine as illustrated generally above in Scheme 1a. However, this method has several drawbacks including a) the toxicity of the starting material, cyanogen, which is currently commercially not available, b) the inconsistent and low yields obtained and c) the need for a laborious recrystallization step to achieve high purity. In addition, the hazards of handling anhydrous hydrazine are well documented in literature.

In another method, one is able to manufacture 3-CNT beginning with 3-chloro-1,2,4-triazole and sodium cyanide as illustrated generally above in Scheme 1c (see, U.K. Patent No. 1,157,256). However this method also has several drawbacks including a) limited supply of the starting material, 3-chloro-1,2,4-triazole, b) the high reaction temperature (150-160° C.) which results in mixture of products which is difficult to work up, and c) low isolated yields.

Cyanoimidazoles

Likewise, multiple routes have been published in the literature for the synthesis of 4(5)-cyanoimidazoles and these have not been commercialized. Methods for preparing cyanoimidazoles are generally reviewed in M. R. Grimmett Science of Synthesis 12: 325-528 (2002). Some of these are discussed in more detail below.

Enaminonitriles have been cyclized into imidazole 4-carbonitrile (see, Ferris and Trimmer, J. Org. Chem. 41(1): 19-24 (1976)). Cyano groups can be introduced onto imidazoles by reacting imidazoles with carbon tetrahalides in liquid ammonia (see, Japanese Patent 59227852). In addition, 4(5)-cyanoimidazoles can be prepared by decarboxylation of cyanoimidazole carboxylic acids by heating, often in the presence of phosphonium or ammonium salt catalysts, such as tetrabutylphosphonium bromide; alkali or alkali earth metal salts, such as lithium chloride (see, Japanese Patent Nos.: 2002322158 and 2002371068); or sequential treatment with metal complexes in protic solvents, alkali hydroxides, ammonia, copper sulfate and sodium hydroxide (see, Japanese Patent Nos.: 03197465 and 2869118). Cyanoimidazoles can be prepared by dehydrating oxime imidazoles with heating in the presence of $Ac_2O$ (see, Japanese Patent Nos.: 62175471 and 2562872 and Kawakami et al. Synthesis 5: 677-680 (2003)). 4(5)-cyanoimidazole can also be prepared by treating 4(5)-trifluoromethylimidazole with 5% $NH_4OH$ (see, Matthews et al. J. Org. Chem. 51(16): 3228-31 (1986)), although the starting material is not readily available. Finally, 4(5)-cyanoimidazole has been prepared from 4(5)-imidazole-carboxaldehyde and 4(5)-thiocarbamoylimidazole, although similarly, both starting materials are not readily available. Of the various other synthetic routes leading to 4-cyanoimidazole described in literature, none are cost effective methods.

Cyanopyrazines

Multiple routes have been published in the literature for the synthesis of 3-cyanopyrazines and these have not been commercialized. Methods for preparing cyanoimidazoles are generally reviewed in N. Sato, Science of Synthesis 16: 751-844 (2004). Some of these are discussed in more detail below.

2-Cyanopyrazine was prepared by oxidation of 2-methylpyrazine with ammonia in the presence of various catalysts. The drawbacks of these method include their requiring a) a specially prepared catalyst, b) a pressure reactor to contain ammonia and oxygen and/or c) high reaction temperatures (>350° C.). (see, Rao et al. Cat. Lett 68(3, 4): 223-227 (2000); Green, Chem. 3(1): 20-22 (2001); Rao et al., Chemical Communications 20: 2088-89 (2001); Rao et al., Indian Patent No. 185,265; Reddy et al., Indian Patent Nos. 182,184 and 182,185; Chinese Patent Nos: 1,398,855 and 1,398,856;

Srilakshmi et al., *Cat. Lett.* 83(3-4): 127-32 (2002); Bondareva et al, *Kinetics and Catalysis* 45(1): 104-113 (2004); 41(5): 670-678 (2000); 41(2): 222-230 (2000); 38(5): 657-661 and 662-668 (1997); *Reaction Kinetics and Catalysis Letters* 79(1): 165-173 (2003); *Catalysis Today* 61(1-4): 173-178 (2000); *Catalysis Lett.* 42(1, 2): 113-118 (1996); Feng et al. *Gaoxiao Huaxue Gongcheng Xuebao* 17(4): 395-399 (2003); Gupta et al. Indian Patent No. 177,142; Jin et al *Jingxi Huagong* 19(6) (2002); Sasaki et al. *Applied Cat., A: General* 194-195: 497-505 (2000) and U.S. Pat. No. 6,392,048); Shin et al. Chem. Technol. Res. Div. 8(5): 749-755 (1997); Gusejnov et al. Russian Patent No. 2061689; Lee et al. U.S. Pat. Nos. 5,786,478 and 6,013,800 and Korean Patent Nos. 151820; Reddy et al. *Chem. Ind.* 62: 487-491 (1995); Lempers et al. *Inorganica Chimica Acta* 225(1-2)67-74 (1994); Wang et al. *Tianranqi Huagong* 18(5): 45-9 (1993); S. Shimizu, *Shkubai* 35(1): 22-6 (1993); *Petrotech* 15(6): 514-18 (1992), U.S. Pat. Nos. 4,778,890 and 4,931,561; Kwon et al *Taehan Hwahakhoe Chi* 34(5): 445-51 (1990); Husain et al. *J. Chrom* 513: 83-91 (1990); L. Forni *J. Chem. Soc., Faraday Trans 1: Physical Chem. Condensed Phases* 84(7): 2397-407 (1988); *Applied Catalysis* 20(1-2):219-30 (1986); Abe et al. Japanese Patent No. 63,010,753; Bergstein et al. U.S. Pat. Nos. 4,419,272 and 4,496,729); Okada et al. *Yakugaku Zasshi* 98(11); (1978); Kajiyama et al. Japanese Patent No. 49030382; Beutel et al. U.S. Pat. No. 3,555,021; Srilaxmi et al. (*Catalysis Comm.* 5: 199-203 (2004); and Narashima et al. (*Chem. Comm.* 20: 2088-2089 (2001).

In addition, Cao et al. (see, *Syn. Comm.* 31(14): 2203-2207 (2001)) describe treating halo-pyrazines neat with sodium cyanide and a phase transfer catalyst. Jose et al. (see *Syn. Comm.* 30(8): 1509-1514 (2000)) describe dehydrating aldoximes with Burgess reagent. Sato et al. (see, *J. Chem. Soc. Perkin Trans I* 11: 2877-81 (1991)) describe treating 3-substituted pyrazine 1-oxides with TMSCN or $(EtO_2)$POCN and triethylamine, optionally in the presence of $ZnBr_2$. This method gives mixtures of products in low yields.

Finally, Zergenyi et al. (European Patent No. 122355) describes treating fluoropyrazine with $Me_2SO$ and NaCN to give pyrazinecarbonitrile. Hardt et al. (see, *J. Analytical and Applied Pyrolysis* 13(3): 191-8 (1988)) describe pyrolyzing polyhydroxyalkylpyrazines with ammonia to give multiple pyrazine products.

Carboxamide to Nitrile Conversions

A common strategy to prepare other nitrile-substituted compounds is to start with the corresponding carboxamide (for reviews see, *Chem. Rev.* 42:189 (1948); *Z. Chem.* 22: 126 (1982)). The carbonyl oxygen can be dehydrated by a number of reaction conditions to form the nitrile functionality as illustrated below in Table 1.

TABLE 1

Formation of Nitriles from Carboxamides

| Reaction Conditions (Reagents, Solvents, Temperature, Time, etc.) | Reference |
|---|---|
| $SOCl_2$ in DMF | *J. Am. Chem. Soc.* 69: 2663 (1947) |
| | *J. Am. Chem. Soc.* 82: 2498 (1960) |
| | *J. Am. Chem. Soc.* 83: 2354 (1961) |
| | *J. Am. Chem. Soc.* 83: 2363 (1961) |
| | *J. Org. Chem.* 27: 4608 (1962) |
| | *Org. Syn.* 4: 436 (1963) |
| | *J. Org. Chem.* 24: 26 (1959) |
| | *J. Org. Chem.* 36: 3960 (1971) |
| | *J. Org. Chem.* 50: 2323 (1985) |
| | *Tetrahedron*. 21: 2239 (1965) |
| | *J. Am. Chem. Soc.* 88: 2025 (1966) |

TABLE 1-continued

Formation of Nitriles from Carboxamides

| Reaction Conditions (Reagents, Solvents, Temperature, Time, etc.) | Reference |
|---|---|
| $ClSO_3NCO$, $Et_3N$ | *Chem. Comm.* 227 (1979) |
| $PhSO_2Cl$ in pyridine | *J. Chem. Soc.* 763 (1946) |
| | *J. Am. Chem. Soc.* 77: 1701 (1955) |
| TsCl, pyridine | *J. Am. Chem. Soc.* 77: 1701 (1955) |
| | *BSCF* 2262 (1965) |
| Sulfurous acid dipyridin-2-yl ester | *Tet. Lett.* 27: 1925 (1986) |
| $(CF_3CO)_2O$, pyridine | *Tet. Lett.* 1813 (1977) |
| $P_2O_5$ with $Me_3SiOSiMe_3$ | *J. Org. Chem.* 27: 4608 (1962) |
| | *Org Synthesis* 4(144): 486 (1963) |
| | *Synthesis* 591 (1982) |
| $(Ph_3PO_3SCF_3)O_3SCF_3$ | *Tetrahedron Lett.* 277 (1975) |
| $(EtO)_2POP(OEt)_2$ | *J. Am. Chem. Soc.* 88: 2025 (1966) |
| $(EtO)_3PI_2$ | *Tetrahedron Lett.* 1725 (1979) |
| 2,2,2-Trichloro-1,3-dioxa-$2\lambda^5$-phosphaindane, pyridine | *J. Am. Chem. Soc.* 88: 2025 (1966) |
| 2-Chloro-[1,3,2]dioxaphospholane | *Ber.* 96: 1387 (1963) |
| $POCl_3$ in DMF, DMF/pyridine or $CH_2ClCH_2Cl$ | *J. Am. Chem. Soc.* 65: 2471 (1943) |
| | *J. Am. Chem. Soc.* 70: 3316 (1948) |
| | *J. Org. Chem.* 27: 4608 (1962) |
| | *J. Org. Chem.* 50: 5451 (1985) |
| | U.S. Pat. No. 2,389,217 |
| | U.S. Pat. No. 4,619,991 |
| | *Syn. Comm.* 10: 479 (1980) |
| | *Org Syn.* 3 535 (1955) |
| $PPh_3$, $CCl_4$ | *Tetrahedron Lett.* 4383 (1970) |
| | *Ber.* 104: 1030 (1971) |
| $Ph_2P$-polymer, $CCl_4$ | *Syn.* 41 (1977) |
| $(PNCl_2)_3$ | *Can. J. Chem.* 50: 3857 (1972) |
| $P(NEt_2)_3$ | *Chem. Lett.* 577 (1973) |
| $COCl_2$, pyridine with DMF | *J. Chem. Soc.* 3730 (1954) |
| | *Syn. Comm.* 10: 479 (1980) |
| ClCOCOCl, DMF, pyridine | *Syn. Comm.* 10: 479 (1980) |
| $ClCO_2Me$ | *Bull. Acad. Polon. Sci.,Ser. Sci. Chem.* 10: 227 (1962) |
| $Cl_3CCOCl$, $Et_3N$ | *Synthesis* 184 (1985) |
| $Cl_3COCOCl$, $OP(OMe)_3$ | *Tetrahedron Lett.* 27: 2203 (1986) |
| $Cl_3CN=CCl_2$ | *Synthesis* 599 (1972) |
| $NaCl \cdot AlCl_3$, $\Delta$ | *J. Am. Chem. Soc.* 62: 1432 (1940) |
| cat. $ClRh(PPh_3)_3$ | *Tetrahedron Lett.* 1963 (1970) |
| $TiCl_4/R_3N$ | *Tetrahedron Lett.* 1501 (1971) |
| $HCCl_3$, NaOH, $PhCH_2NEt_3)^+Cl^-$ | *Tetrahedron Lett.* 2121 (1973) |
| $HN(SiMe_2)_{3\ or\ 4}$ | *J. Org. Chem.* 35: 3253 (1970) |
| 2,4,6-Trichloro-1,3,5-triazine, DMF | *Synthesis* 657 (1980) |
| DCC, pyridine | *J. Org. Chem.* 26: 3356 (1961) |
| | *J. Org. Chem.* 36: 3960 (1971) |
| | *J. Am. Chem. Soc.* 88: 2025 (1966) |
| $LiAlH_4$ | *Can. J. Chem.* 44: 2113 (1966) |

These include commercial scale processes using thionyl chloride ($SOCl_2$), phosphorous oxychloride ($POCl_3$) or trifluoroacetic acid anhydride (TFAA) in solvents such as DMF and pyridine to convert the carboxamide to the corresponding nitrile (see Table 1). For instance, dehydration of cyanoacetamide with $POCl_3$ in ethylene dichloride or benzene produces malonitrile in 70-80% yield (see, Surrey, et al., U.S. Pat. No. 2,389,217). However, the commercial dehydration of carboxamide substituents on nitrogen-containing heteroaryl compounds using these methods presents serious challenges. Most notable is general insolubility of these starting materials in solvents compatible with the dehydrating agents and by-products formation. For instance, dehydration of 5-amino-4-carboxamido-1,2,3-triazole with $POCl_3$ in DMF requires protection of the 5-amino group and the 1-N of the triazole to effect the dehydration in 60% yield (see Mattzinger, et al., U.S. Pat. No. 4,619,991). Likewise dehydration of 4(5)-imidazole-carboxamide uses dichlorophenylphosphine oxide as a dehydrating agent to give 4-cyanoimidazole (see Leone-Bay and Glaser *Syn. Comm.* 17(12): 1409-12 (1987)). Dichlorophenylphosphine oxide is not readily available and is relatively expensive. Finally, dehydration of pyrazineamide uses neat phosphoryl chloride as a dehydrating agent to give 2-cyanopyrazine (see, Johnston U.S. Pat. No. 4,442,097). No solvent is used.

In contrast, the preparation of cyano-substituted-nitrogen-containing heteroaryl compounds is much more difficult. This is mainly due to the poor solubility of carboxamide-substituted nitrogen-containing heteroaryl compounds in typical dehydration solvents. Slight increase in the yield is achieved when the reaction solvent is MEK as compared with no solvent. Other dehydration agents, such as $SOCl_2$ and trifluoroacetic anhydride, etc., under a variety of reaction conditions, also fail to provide product in reasonable yields (ca. >20%). In fact, a perusal of the literature supports the observation that the use of substrate insoluble solvents reduces the yield.

In addition, the quality of the products are sensitive to conditions for its formation, including the scale of the reaction. This in turn has an impact on the quality and yield of the final products which is important for launch of a compound to market.

What is needed in the art are methods that allow one to reliably produce cyano-substituted-nitrogen-containing heteroaryl compounds from carboxamide-substituted-nitrogen-containing heteroaryl compounds in one step and in high yields without laborious purification. Quite surprisingly, the present invention fulfills these and other needs.

SUMMARY OF THE INVENTION

The present invention provides dehydration methods that can be used to convert the carboxamide-substituted, nitrogen-containing heteroaryl compounds, to the corresponding cyano-substituted, nitrogen-containing heteroaryl compounds. Using the methods of the present invention, the cyano-substituted, nitrogen-containing heteroaryl compounds can be prepared reliably, in high yields and in high purity. In particular, the methods of the present invention improves 1) scalability of the method, particularly by improving the stirrability of reactions by using solvents, co-solvents, and organic bases; 2) robustness, particularly with regard to the quench and work-up and product/intermediate isolation for a step-wise process, and 3) efficiency, economy, and environmental impact.

As such, in one embodiment, the present invention provides a method for preparing a compound having the following general Formula I:

$$R^1\text{—CN} \qquad (I)$$

or a tautomer or salt thereof, said method comprising dehydrating a compound having the following general Formula II:

$$R^1\text{—CXNH}_2, \qquad (II)$$

under conditions appropriate to form a compound of Formula I, and optionally, producing a salt, solvate or hydrate thereof. In the above formula, X is O or S. In the above formula, $R^1$ is a nitrogen-containing-heteroaryl group. Examples of nitrogen-containing heteroaryl groups, include, but are not limited to, a triazolyl group, an imidazolyl group, a pyrroyl group, a pyrazinyl group, a pyridinyl group and a pyrimidinyl group and the like. In one group of embodiments, the nitrogen-containing heteroaryl group is a triazolyl group, an imidazolyl group and a pyrazinyl group. Each nitrogen-containing heteroaryl group is optionally substituted with from 1 to 2 substituents independently selected from the group consisting of $C_{1-8}$alkyl, aryl and halogen. In one group of embodiments, the dehydrating agent is a member selected from the group consisting of thionyl chloride ($SOCl_2$), phosphorus oxychloride ($POCl_3$) and trifluoroacetic anhydride (TFAA). In one group of embodiments, the dehydrating agent is present in an amount ranging from: a) about 2.5 equivalents to about 9 equivalents to the amount of the compound of Formula II; b) about 3 equivalents to about 8.5 equivalents to the amount of the compound of Formula II; c) about 3.5 equivalents to about 8 equivalents to the amount of the compound of Formula II; d) about 4 equivalents to about 7.5 equivalents to the amount of the compound of Formula II; e) about 4.5 equivalents to about 7 equivalents to the amount of the compound of Formula II; f) about 5 equivalents to about 6.5 equivalents to the amount of the compound of Formula II; or g) about 5.5 equivalents to about 6 equivalents to the amount of the compound of Formula II. In one group of embodiments, the dehydrating agent is present at a concentration ranging from: a) about 3 molar equivalents to 28 molar equivalents to the amount of the compound of Formula I; b) about 6 molar equivalents to 25 molar equivalents to the amount of the compound of Formula I; c) about 9 molar equivalents to 22 molar equivalents to the amount of the compound of Formula I; d) about 12 molar equivalents to 19 molar equivalents to the amount of the compound of Formula I; or e) about 15 molar equivalents to 16 molar equivalents to the amount of the compound of Formula I. In another group of embodiments, the mixture includes an organic base soluble in the mixture. In one group of embodiments, the dehydration is carried out in a solvent selected from the group consisting of acetonitrile, 1,4-dioxane, ethyl acetate, 1-methyl-2-pyrrolidinone, pyridine and the like. In one group of embodiments, the solvent is acetonitrile. In one group of embodiments, the dehydration is carried out at a temperature ranging from: a) about 0° C. to about 160° C.; b) about 25° C. to about 135° C.; c) about 50° C. to about 110° C.; or d) about 75° C. to about 85° C. In one group of embodiments, $R^1$ is a 1,2,4-triazo-3-yl group or imidazo-4-yl group or pyrazin-2-yl group; the dehydrating agent is $POCl_3$; and the solvent is acetonitrile.

In another embodiment, the reaction mixture is distilled to recover $POCl_3$ and solvent for recycle, quenched with a quenching agent selected from the group consisting of water, aqueous caustic medium and alkylamines. In another embodiment, the cyano-substituted-nitrogen-containing heterocycle is worked up by extraction or filtration. In a preferred embodiment, extraction comprises contacting the reaction mixture with a solvent selected from the group consisting of ethyl acetate, isopropyl acetate, diethyl ether, 2-methyltetrahydrofuran and methylene chloride. In another preferred embodiment, filtration comprises contacting the compound of Formula I with a solvent in which the compound of Formula I is insoluble and filtering the mixture to provide purified compound of Formula I. In a presently preferred embodiment, the solvent in which the compound of Formula I is insoluble is toluene.

Other aspects, objects, features and advantages of the present invention would be apparent to one of ordinary skill in the art from the following detailed description illustrating the preferred embodiments of the invention.

DETAILED DESCRIPTION OF THE INVENTION

I. Definitions

As used herein, the following terms have the meanings ascribed to them unless specified otherwise.

In accordance with the present invention and as used herein, the following terms are defined with the following meanings, unless explicitly stated otherwise.

It is noted here that as used in this specification and the appended claims, the singular forms "a," "an," and "the" include plural reference unless the context clearly dictates otherwise.

The phrase "about" as used herein means variation one might see in measurements taken among different instruments, samples, and sample preparations.

The term "compound" as used herein is intended to encompass not only the specified molecular entity but also its pharmaceutically acceptable, pharmacologically active derivatives, including, but not limited to, salts, conjugates such as esters and amides, metabolites, hydrates, solvates and the like.

The term "solvate" as used herein means a compound of the invention or a salt, thereof, that further includes a stoichiometric or non-stoichiometric amount of a solvent bound by non-covalent intermolecular forces in an amount of greater than about 0.3% when prepared according to the invention.

The term "solvent" as used herein means a liquid which is capable of dissolving another substance.

The term "hydrate" as used herein means a compound of the invention or a tautomer or salt thereof, that further includes a stoichiometric or non-stoichiometric amount of water bound by non-covalent intermolecular forces. Hydrates are formed by the combination of one or more molecules of water with one of the substances in which the water retains its molecular state as $H_2O$, such combination being able to form one or more hydrate.

The term "anhydrous" as used herein means a compound of the invention or a tautomer or salt thereof that contains less than about 3% by weight water or solvent when prepared according to the invention.

The term "drying" as used herein means a method of removing solvent and/or water from a compound of the invention which, unless otherwise specified, may be done at atmospheric pressure or under reduced pressure and with or without heating until the level of solvent and/or water contained reached an acceptable level.

The term "dehydration" as used herein means a method of removing a hydroxyl functional group from a compound of the invention which, unless otherwise specified, may be done under any suitable reaction conditions.

"Alkyl," by itself or as part of another substituent, means, unless otherwise stated, a straight or branched chain, fully saturated aliphatic hydrocarbon radical having the number of carbon atoms designated. For example, "$C_{1-8}$alkyl" refers to a hydrocarbon radical straight or branched, containing from 1 to 8 carbon atoms that is derived by the removal of one hydrogen atom from a single carbon atom of a parent alkane. The phrase "unsubstituted alkyl" refers to alkyl groups that do not contain groups other than fully saturated aliphatic hydrocarbon radicals. Thus, the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups such as isopropyl, t-butyl, isobutyl, sec-butyl, and the like. Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms.

"Aryl" by itself or as part of another substituent refers to a polyunsaturated, aromatic, hydrocarbon group containing from 6 to 14 carbon atoms, which can be a single ring or multiple rings (up to three rings) which are fused together or linked covalently. Thus the phrase includes, but is not limited to, groups such as phenyl, biphenyl, anthracenyl, naphthyl by way of example. Non-limiting examples of unsubstituted aryl groups include phenyl, 1-naphthyl, 2-naphthyl and 4-biphenyl.

"Heteroaryl" refers to a cyclic or polycyclic aromatic radical that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom or through a carbon atom and can contain 5 to 10 carbon atoms. Non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl and 4-pyrimidyl. If not specifically stated, substituents for each of the above noted aryl and heteroaryl ring systems are selected from the group of acceptable substituents described herein. "Substituted heteroaryl" refers to an unsubstituted heteroaryl group as defined above in which one or more of the ring members are bonded to a non-hydrogen atom such as described above with respect to substituted alkyl groups and substituted aryl groups. Representative substituents include straight and branched chain alkyl groups —$CH_3$, —$C_2H_5$, —$CH_2OH$, —$OH$, —$OCH_3$, —$OC_2H_5$, —$OCF_3$, —$OC(=O)CH_3$, —$OC(=O)NH_2$, —$OC(=O)N(CH_3)_2$, —$CN$, —$NO_2$, —$C(=O)CH_3$, —$CO_2H$, —$CO_2CH_3$, —$CONH_2$, —$NH_2$, —$N(CH_3)_2$, —$NHSO_2CH_3$, —$NHCOCH_3$, —$NHC(=O)OCH_3$, —$NHSO_2CH_3$, —$SO_2CH_3$, —$SO_2NH_2$ and halo.

In each of the above embodiments designating a number of atoms, e.g. "$C_{1-8}$," is meant to include all possible embodiments that have one fewer atom. Non-limiting examples include $C_{1-7}$, $C_{2-8}$, $C_{2-7}$, $C_{3-8}$, $C_{3-7}$ and the like.

Each of the terms herein (e.g., "alkyl," "heteroalkyl," "aryl" and "heteroaryl") is meant to include both "unsubstituted" and optionally "substituted" forms of the indicated radical, unless otherwise indicated. Typically each radical is substituted with 0, 1, 2 3 4 or 5 substituents, unless otherwise indicated. Examples of substituents for each type of radical are provided below.

"Substituted" refers to a group as defined herein in which one or more bonds to a carbon(s) or hydrogen(s) are replaced by a bond to non-hydrogen and non-carbon atom "substituents" such as, but not limited to, a halogen atom such as F, Cl, Br, and I; an oxygen atom in groups such as hydroxyl groups, alkoxy groups, aryloxy, and acyloxy groups; a sulfur atom in groups such as thiol groups, alkyl and aryl sulfide groups, sulfone groups, sulfonyl groups, and sulfoxide groups; a nitrogen atom in groups such as amino, alkylamines, dialkylamines, arylamines, alkylarylamines, diarylamines, alkoxyamino, hydroxyamino, acylamino, sulfonylamino, N-oxides, imides, and enamines; and other heteroatoms in various other groups. "Substituents" also include groups in which one or more bonds to a carbon(s) or hydrogen(s) atom is replaced by a higher-order bond (e.g., a double- or triple-bond) to a heteroatom such as oxygen in oxo, acyl, amido, alkoxycarbonyl, aminocarbonyl, carboxyl, and ester groups; nitrogen in groups such as imines, oximes, hydrazones, and nitriles. "Substituents" further include groups in which one or more bonds to a carbon(s) or hydrogen(s) atoms is replaced by a bond to a cycloalkyl, heterocyclyl, aryl, and heteroaryl groups. Representative "substituents" include, among others, groups in which one or more bonds to a carbon or hydrogen atom is/are replaced by one or more bonds to fluoro, chloro, or bromo group. Another representative "substituent" is the trifluoromethyl group and other groups that contain the trifluoromethyl group. Other representative "substituents" include those in which one or more bonds to a carbon or hydrogen atom is replaced by a bond to an oxygen atom such that the substituted alkyl group contains a hydroxyl, alkoxy, or aryloxy group. Other representative "substituents" include alkyl groups that have an amine, or a substituted or unsubstituted alkylamine, dialkylamine, arylamine, (alkyl)(aryl)amine, diarylamine, heterocyclylamine, diheterocyclylamine, (alkyl)(heterocyclyl)amine, or (aryl)(heterocyclyl)amine group. Still other representative "substituents" include those in which one or more bonds to a carbon(s) or hydrogen(s) atoms is replaced by a bond to an alkyl, cycloalkyl, aryl, heteroaryl, or heterocyclyl group.

The herein-defined groups may include prefixes and/or suffixes that are commonly used in the art to create additional well-recognized substituent groups. As examples, "alkylamino" refers to a group of the formula —$NR^aR^b$. Unless stated otherwise, for the following groups containing $R^a$, $R^b$, $R^c$, $R^d$ and $R^e$: $R^a$, and $R^b$ are each independently selected from H, alkyl, alkoxy, thioalkoxy, cycloalkyl, aryl, heteroaryl, or heterocyclyl or are optionally joined together with the atom(s) to which they are attached to form a cyclic group. When $R^a$ and $R^b$ are attached to the same nitrogen atom, they can be combined with the nitrogen atom to form a 5-, 6- or 7-membered ring. For example, —$NR^aR^b$ is meant to include 1-pyrrolidinyl and 4-morpholinyl.

$R^c$, $R^d$, $R^e$ and $R^f$ are each independently selected from alkyl, alkenyl, alkynyl, cycloalkyl, cycloalkenyl, aryl, heteroaryl, heterocyclyl or alkylenearyl as defined herein.

Typically, a particular radical will have 0, 1, 2 or 3 substituents, with those groups having two or fewer substituents being preferred in the present invention. More preferably, a radical will be unsubstituted or monosubstituted. Most preferably, a radical will be unsubstituted.

Examples of substituted alkyl are: —$(CH_2)_3NH_2$, —$(CH_2)_3NH(CH_3)$, —$(CH_2)_3NH(CH_3)_2$, —$CH_2C(=CH_2)$ $CH_2NH_2$, —$CH_2C(=O)CH_2NH_2$, —$CH_2S(=O)_2CH_3$, —$CH_2OCH_2NH_2$, —$CO_2H$. Examples of substituents of substituted alkyl are: $CH_2OH$, —OH, —$OCH_3$, —$OC_2H_5$, —$OCF_3$, —$OC(=O)CH_3$, —$OC(=O)NH_2$, —$OC(=O)N$ $(CH_3)_2$, —CN, —$NO_2$, —$C(=O)CH_3$, —$CO_2H$, —$CO_2CH_3$, —$CONH_2$, —$NH_2$, —$N(CH_3)_2$, —$NHSO_2CH_3$, —$NHCOCH_3$, —$NHC(=O)OCH_3$, —$NHSO_2CH_3$, —$SO_2CH_3$, —$SO_2NH_2$, and halo.

Similarly, "substituents" for the aryl and heteroaryl groups are varied and are selected from: -halogen, —$OR^a$, —$OC(O)R^a$, —$NR^aR^b$, —$SR^a$, —$R^a$, —CN, —$NO_2$, —$CO_2R^a$, —$CONR^aR^b$, —$C(O)R^a$, —$OC(O)NR^aR^b$, —$NR^bC(O)R^a$, —$NR^bC(O)_2R^a$, —$NR^a$—$C(O)NR^bR^c$, —NH—$C(NH_2)$ =NH, —$NR^aC(NH_2)$=NH, —NH—$C(NH_2)$=$NR^a$, —$S(O)R^a$, —$S(O)_2R^a$, —$S(O)_2NR^aR^b$, —$N_3$, —$CH(Ph)_2$, perfluoro$C_{1-8}$alkoxy, and perfluoro$C_{1-8}$alkyl, in a number ranging from zero to the total number of open valences on the aromatic ring system; and where $R^a$, $R^b$ and $R^c$ are independently selected from hydrogen, alkyl and heteroalkyl, unsubstituted aryl and heteroaryl, (unsubstituted aryl)-$C_{1-8}$alkyl, and (unsubstituted aryl)oxy-$C_{1-8}$alkyl.

"Cyano" refers to —CN.

"Halo" or "halogen" by themselves or as part of another substituent, mean, unless otherwise stated, a fluorine, chlorine, bromine, or iodine atom. Additionally, terms such as "haloalkyl", are meant to include alkyl in which one or more hydrogen is substituted with halogen atoms which can be the same or different, in a number ranging from one up to the maximum number of halogens permitted e.g. for alkyl, (2 m'+1), where m' is the total number of carbon atoms in the alkyl group. For example, the term "halo$C_{1-8}$alkyl" is meant to include trifluoromethyl, 2,2,2-trifluoroethyl, 4-chlorobutyl, 3-bromopropyl, and the like. The term "perhaloalkyl" means, unless otherwise stated, alkyl substituted with (2 m'+1) halogen atoms, where m' is the total number of carbon atoms in the alkyl group. For example, the term "perhalo$C_{1-8}$alkyl", is meant to include trifluoromethyl, pentachloroethyl, 1,1,1-trifluoro-2-bromo-2-chloroethyl, and the like. Additionally, term "haloalkoxy" refers to an alkoxy radical substituted with one or more halogen atoms.

"Hydroxy" or "hydroxyl" refers to the group —OH.

The terms "optional" or "optionally" as used throughout the specification means that the subsequently described event or circumstance may but need not occur, and that the description includes instances where the event or circumstance occurs and instances in which it does not. For example, "heterocyclo group optionally mono- or di-substituted with an alkyl group means that the alkyl may but need not be present, and the description includes situations where the heterocyclo group is mono- or disubstituted with an alkyl group and situations where the heterocyclo group is not substituted with the alkyl group.

"Optionally substituted" means a ring which is optionally substituted independently with substituents. A site of a group that is unsubstituted may be substituted with hydrogen.

As used herein, the term "organic base" refers to an organic substance that can accept protons, or a substance that is an electron pair donor. Organic bases useful in the present invention include amines. Exemplary bases include, but are not limited to, triethylamine, diisopropylethylamine, pyridine and N-methyl morpholine. One of skill in the art will appreciate that other bases are useful in the present invention.

The term "salt" include salts of compounds derived from the combination of a compound and an organic or inorganic acid. These compounds are useful in both free base and salt form. In practice, the use of the salt form amounts to use of the base form; both acid and base addition salts are within the scope of the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The term "tautomer" means compounds produced by the phenomenon wherein a proton of one atom of a molecule shifts to another atom. See, Jerry March, Advanced Organic Chemistry: Reactions, Mechanisms and Structures, Fourth Edition, John Wiley & Sons, pages 69-74 (1992). The tautomers also refer to one of two or more structural isomers that exist in equilibrium and are readily converted from one isomeric form to another. Examples of include keto-enol tautomers, such as acetone/propen-2-ol and the like, ring-chain tautomers, such as glucose/2,3,4,5,6-pentahydroxy-hexanal, aromatic tautomers and the like. The compounds described herein may have one or more tautomers and therefore include various isomers. All such isomeric forms of these compounds are expressly included in the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

II. Method of the Invention

The present invention provides dehydration methods that can generally and reliably be used to prepare cyano-substituted-nitrogen-containing heteroaryl compounds from carboxamide-substituted-nitrogen-containing heteroaryl starting materials in high yields.

Quite surprisingly and in contrast to the teachings of both the scientific and patent literature, it has now been discovered that the dehydration of carboxamide-substituted nitrogen-containing heteroaryl compounds proceeds with high yields when a dehydrating agent selected from the group consisting of trifluoroacetic anhydride, thionyl chloride, and phosphorus oxychloride is used in a solvent selected from the group consisting of acetonitrile, 1,4-dioxane, 1-methyl-2-pyrrolidinone, trifluoroacetic anhydride, and pyridine. These high yields are unusual since dehydration of similar compounds with similar dehydrating agent in other solvents do not result in high yields (e.g., see, Table 1 above).

As such, in one embodiment, the present invention provides a method for preparing a compound having the following general Formula I:

R—CN   (I)

or a tautomer or salt thereof,
the method comprising dehydrating a compound having the following general Formula II:

R—CXNH$_2$   (II)

with a dehydrating agent in a compatible solvent.

In the above formulae, X is a group that is converted to a leaving group upon treatment with the dehydrating agent. Suitable leaving groups will be readily apparent to those of skill in the art. In one embodiment, X is O or S. In another embodiment, X is O.

In the above formulae, R$^1$ is nitrogen-containing heteroaryl group. More particularly, in the above formulae, R$^1$ is selected from the group consisting of a triazolyl, an imidazolyl, a pyrroyl, a pyrazinyl, a pyridinyl and a pyrimidinyl group.

As such, in one embodiment, the compound of Formulae I and II is selected from the group consisting of:

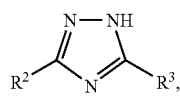   (a)

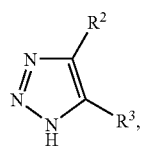   (b)

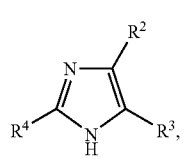   (c)

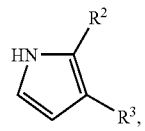   (d)

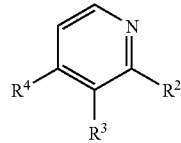   (e)

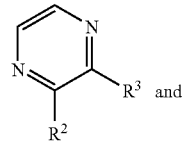   (f)

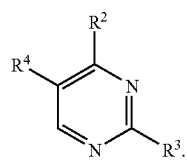   (g)

or a tautomer or salt thereof; wherein each R$^2$, R$^3$ and R$^4$ is independently selected from the group consisting of H, C$_{1-8}$alkyl, aryl and halogen, wherein exactly one of R$^2$, R$^3$ and R$^4$ is CN in Formula I and the same R$^2$, R$^3$ or R$^4$ is CONH$_2$ in Formula II.

In another group of embodiments, the compound of Formula I is selected from the group consisting of:

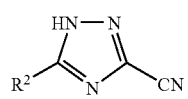   (Iai)

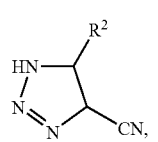   (Ibi)

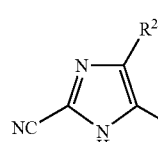   (Ibii)

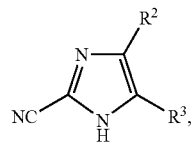   (Ici)

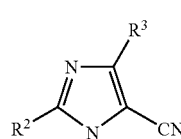   (Idi)

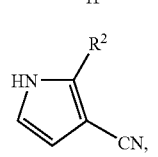

-continued

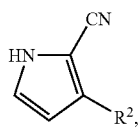
(Idii)

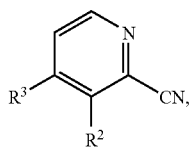
(Iei)

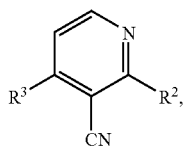
(Ieii)

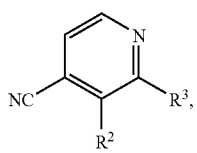
(Ieiii)

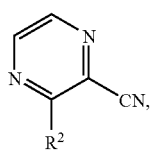
(Ifi)

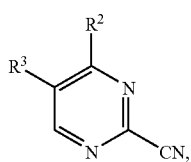
(Igi)

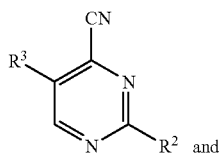
(Igii)

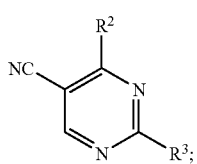
(Igiii)

or a tautomer or salt thereof; wherein each $R^2$, $R^3$ and $R^4$ are independently selected from the group consisting of H, $C_{1-8}$alkyl, aryl and halogen.

In another group of embodiments, the compound of Formula Iai has the structure:

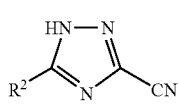
(Iai)

wherein $R^2$ is selected from the group consisting of H, $C_{1-8}$alkyl, aryl and halogen; or a tautomer or salt thereof. The compound is prepared by dehydrating a compound having the following Formula IIai:

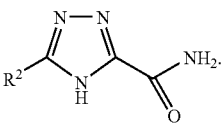
(IIai)

In another group of embodiments, the compound of Formula I has the following Formula Ici:

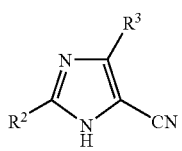
(Ici)

wherein $R^2$ is selected from the group consisting of H, $C_{1-8}$alkyl, aryl and halogen; or a tautomer or salt thereof, and the compound is prepared by dehydrating a compound having the following Formula IIci:

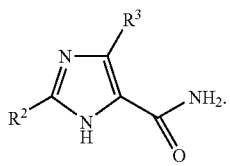
(IIci)

In another group of embodiments, the compound has the following Formula Ifi:

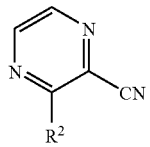
(Ifi)

wherein $R^2$ is selected from the group consisting of H, $C_{1-8}$alkyl, aryl and halogen; or a tautomer or salt thereof, and the compound is prepared by dehydrating a compound having the following Formula IIfi:

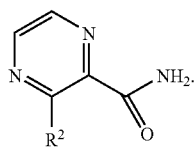
(IIfi)

Within any of the groups of embodiments herein, $R^2$ and $R^3$ may be H.

In another group of embodiments, a nitrogen of the nitrogen-containing heteroaryl group may be blocked or protected. Suitable nitrogen blocking groups include, for example, those known to be useful in the art of stepwise synthesis of nitrogen-containing heteroaryl compounds. These include, but are not limited to, acyl type protecting groups (e.g., formyl, trifluoroacetyl, acetyl, etc.), aromatic urethane type protecting groups (e.g., benzyloxycarboyl (Cbz), substituted Cbz, etc.), aliphatic urethane type protecting groups (e.g., t-butyloxycarbonyl (Boc), isopropylcarbonyl, cyclohexyloxycarbonyl, etc.) and alkyl type protecting groups (e.g., benzyl, triphenylmethyl, etc.) (see Greene et al. *Protective Groups in Organic Synthesis*). In a presently preferred embodiment, the nitrogen is not blocked or protected.

Examples of dehydrating agents suitable for use in the methods of the present invention include, but are not limited to, thionyl chloride ($SOCl_2$), phosphorus oxychloride ($POCl_3$) and trifluoroacetic anhydride (TFAA). In a presently preferred embodiment, the dehydrating agent is $POCl_3$. Phosphorus oxychloride, thionyl chloride, and trifluoroacetic anhydride are commercially available as clear liquids and may be used neat.

In one embodiment, the dehydration is preferably carried out in a compatible solvent. A compatible solvent is one which is compatible with the dehydration reaction and can readily dissolve carboxamide-substituted nitrogen-containing heteroaryl compounds. Exemplar solvents include, but are not limited, to the following: acetonitrile, 1,4-dioxane, 1-methyl-2-pyrrolidinone, trifluoroacetic anhydride, pyridine and mixtures thereof.

The solubility of 3-CNT among these solvents may be relatively lower and a larger amount is needed to dissolve 3-CNT, thereby reducing reactor efficiency to some extent. The reactor efficiency can be improved by either using acetonitrile as the sole solvent or adding acetonitrile as a secondary solvent. The reaction rates may be affected accordingly based on the reflux temperatures of the solvents with the above modifications.

In another embodiment, the present invention provides a method for preparing 3-CNT, 4-cyano-imidazole and 2-cyanopyrazine. Schemes 2, 3 and 4 illustrate general reaction schemes that can be used to prepare 3-CNT, 4-cyano-imidazole and 2-cyano-pyrazine using the dehydration methods of the invention.

Scheme 2. Synthesis of 3-CNT by Dehydration

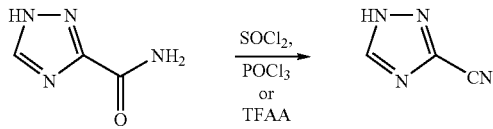

Scheme 3. Synthesis of 4-Cyano-imidazole by Dehydration

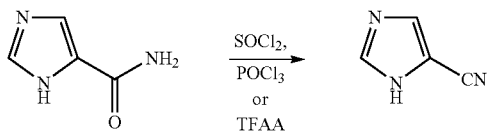

Scheme 4. Synthesis of 2-Cyano-pyrazine

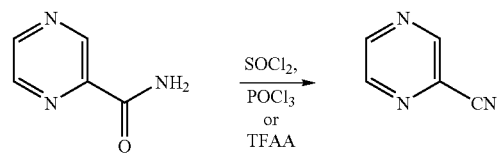

Quite surprisingly, it has been found that the yields for the dehydration of 3-CNT is dependent on the solvent employed. For instance, when methyl ethyl ketone (MEK) is used as the solvent, a 35% yield is obtained. However, when acetonitrile is used as the solvent the overall yield is increased to greater than about 83%.

While not being bound by theory, based on these results, it is thought that a variety of factors, such as salvation, reaction temperature and relative reactivity of the dehydration reagent are responsible for the high yields observed in the $POCl_3$ dehydration of 3-CAT. Thus, as judged on the basis of yield, when $POCl_3$ is used as the dehydrating agent, acetonitrile is preferably used as the solvent.

Appropriate temperatures for conducting particular reaction steps are readily discernable by persons of ordinary skill in the art, for example by monitoring the speed of reaction, solubility of reaction components, and the like. Suitable dehydration conditions include dehydrating the compound at a temperature ranging from: a) about 0° C. to about 160° C.; b) about 25° C. to about 135° C.; c) about 50° C. to about 110° C.; or d) about 75° C. to about 85° C. Suitable dehydration temperatures include room temperature. At lower temperatures, larger amounts of solvent may be needed to maintain homogeneity and dehydration rate. At 75-85° C., the dehydration reaction is rapid and is complete in less than 15 hours. It will be readily apparent to those of skill in the art that the progress of the dehydration reaction can be monitored by, for example, HPLC, and the reaction is deemed complete when the amount of unreacted 3-CAT or other compound of Formula II is less than about 1%.

In addition in certain embodiments, the use of an organic base in the solvent mixture makes the reaction mixture more easily stirrable throughout the reaction. The stoichiometry of the organic base is not particularly important. In one embodiment, an excess of this base is used. Suitable organic bases include, but are not limited to, pyridine and the like.

By using acetonitrile, 1,4-dioxane, ethyl acetate, 1-methyl-2-pyrrolidinone, or pyridine as the solvent in the present invention, it is not necessary to use another solvent to quench and work-up the reaction. Due to these improvements, there is no need to use a large excess of dehydrating agent in the process. In one group of embodiments, the dehydrating agent is present in an amount ranging from: a) about 2.5 equivalents to about 9 equivalents to the amount of the compound of Formula II; b) about 3 equivalents to about 8.5 equivalents to the amount of the compound of Formula II; c) about 3.5 equivalents to about 8 equivalents to the amount of the compound of Formula II; d) about 4 equivalents to about 7.5 equivalents to the amount of the compound of Formula II; e) about 4.5 equivalents to about 7 equivalents to the amount of the compound of Formula II; f) about 5 equivalents to about 6.5 equivalents to the amount of the compound of Formula II; or g) about 5.5 equivalents to about 6 equivalents to the amount of the compound of Formula II. In one group of embodiments, the dehydrating agent is present at a concentration ranging from: a) about 3 molar equivalents to 28 molar equivalents to the amount of the compound of Formula I; b)

about 6 molar equivalents to 25 molar equivalents to the amount of the compound of Formula I; c) about 9 molar equivalents to 22 molar equivalents to the amount of the compound of Formula I; d) about 12 molar equivalents to 19 molar equivalents to the amount of the compound of Formula I; or e) about 15 molar equivalents to 16 molar equivalents to the amount of the compound of Formula I.

The order of addition of solid starting materials, reagents, bases and/or solvents and temperature is not particularly important. This allows even rapid addition of dehydrating agent and warming of the reaction mixture at rates achievable on a production scale without significant safety concerns.

The products and starting materials can be detected by HPLC. Identifying products and starting materials by HPLC is beneficial to determine the endpoint of the reaction.

Because 6.0 equivalents of acid are generated from the reaction of $POCl_3$ with water, enough quenching agent should be used to bring the pH to the desired level. Suitable quenching agents will not react with the products or intermediates and will provide a stable pH. Suitable quenching agents, include but are not limited to, water, $NaHCO_3$, $Na_2CO_3$, NaOH, KOH, $NH_4OH$, triethylamine, and the like and combinations thereof. In one embodiment, about 7 to about 8 equivalents of quenching agent relative to dehydrating agent may be used. The quenching agent may be used in combination with suitable solvents.

The temperature of the reaction mixture during quenching is not particularly important; however it is preferable to keep the temperature from about 0° C. to about 10° C. In one embodiment, the quenching temperature is from about 15° C. to about 35° C. In another embodiment, the quenching temperature is room temperature.

The importance of the sequence of combining the reaction mixture with the quenching agent is independent of the quenching agent used. In one embodiment, the quenching agent is added to the reaction mixture. In another embodiment, the reaction mixture is added to the reaction mixture.

The desired compounds in the methods described herein can be isolated and purified by purification methods conventionally used in organic synthetic chemistry, for example, neutralization, filtration, extraction, washing, drying, concentration, recrystallization, and various kinds of chromatography. The intermediates may be subjected to the subsequent reaction without purification. Thus, in one embodiment, the present invention provides a method for isolating cyano-substituted-nitrogen-containing heteroaryl compounds. Cyano-substituted-nitrogen-containing heteroaryl compounds are generally crystalline and are relatively easy to purify. Cyano-substituted-nitrogen-containing heteroaryl compounds can be isolated by standard purification techniques including, but not limited to, extraction, filtration and recrystallization and by chromatographic methods.

It has been discovered that cyano-substituted-nitrogen-containing heteroaryl compounds have variable solubility in organic solvents and can be separated from a reaction mixture on the basis of their differential solubility. For example, 3-CNT is soluble in hot acetonitrile, whereas it is not soluble in toluene. As such, the present invention provides a method for isolating cyano-substituted-nitrogen-containing heteroaryl compounds from a reaction mixture containing a dehydrating agent, the method comprising: distillation of excess dehydrating agent, neutralization, extracting the reaction mixture with ethyl acetate, drying the organic extracts; distillation of ethyl acetate, adding toluene to produce a particulate suspension, and filtering the suspension to recover the cyano-substituted-nitrogen-containing heterocycle.

For instance, after work up, a crude reaction mixture consisting of 80-90%3-CNT and 0-10% 3-CAT, was extracted with ethyl acetate and the resulting ethyl acetate extractant was dried, filtered, and concentrated. The resulting mixture was quenched by treatment with toluene which was then filtered to provide about 99% pure 3-CNT in >83% yield. A variety of extraction solvents can be used including, but not limited to, ethyl acetate, isopropyl acetate, methylene chloride, 2-methyltetrahydrofuran and the like. In a preferred embodiment, ethyl acetate is used to extract the 3-CNT reaction mixture. A variety of solvents can be used to precipitate 3-CNT including, but not limited to toluene, hexane, heptane and the like. In a preferred embodiment, toluene is used to precipitate 3-CNT.

One benefit to isolating a compound of Formula I is to have a better control over the quality of this intermediate. In another embodiment, a compound of Formula I can be used directly in a subsequent step.

In the case where a salt of a compound of Formula I is desired and the compound is produced in the form of the desired salt, it can be subjected to purification as such. In the case where a compound of Formula I is produced in the free state and its salt is desired, the compound of Formula I is dissolved or suspended in a suitable organic solvent, followed by addition of an acid or a base to form a salt.

Also, the compounds of Formula I and salts thereof may exist in anhydrous form or in the form of adducts with water (hydrates) or various solvents, which are also within the scope of the present invention.

The temperature of the mixtures during these purification procedures is not particularly important; however it is preferable to maintain the solubility of reaction products using solution phase purification techniques, e.g., extraction if the solution is to be transferred to a different reaction vessel for distillation. It will be readily apparent to those of skill in the art that the foregoing discussions relating to nitrogen-containing heteroaryl compounds and their preferred embodiments are fully applicable to these methods.

The following non-limiting examples are provided to better illustrate the present invention. The examples are not intended to limit the scope of the present invention and they should not be so interpreted. Amounts are in weight parts or weight percentages unless otherwise indicated. All of the cited patents and publications are incorporated herein by reference. The following specific examples are provided to better assist the reader in the various aspects of practicing the present invention. As these specific examples are merely illustrative, nothing in the following descriptions should be construed as limiting the invention in any way. Other procedures and adaptations will be apparent to one of ordinary skill in the art upon views these reaction schemes and the structures of the compounds according to the invention. Such procedures are deemed to be within the scope of the present invention.

EXAMPLES

General Methods

The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, 1967-2004, Volumes 1-22; Rodd's Chemistry of Carbon Compounds, Elsevier Science Publishers, 1989, Volumes 1-5 and Supplementals; and Organic Reactions, Wiley & Sons: New York, 2005, Volumes 1-65. The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. to about 75° C.

Referring to the examples that follow, compounds of the present invention were synthesized using the methods described herein, or other methods, which are well known in the art.

The compounds and/or intermediates were characterized by high performance liquid chromatography (HPLC). TLC results were readily detected visually under ultraviolet light, or by employing well known iodine vapor and other various staining techniques.

Mass spectrometric analysis was performed on LCMS instruments.

Nuclear magnetic resonance (NMR) analysis was performed on some of the compounds with a 300 MHz NMR (Palo Alto, Calif.). The spectral reference was either TMS or the known chemical shift of the solvent.

The purity of some of the invention compounds is assessed by differential scanning calorimeter (DSC).

Melting points are determined on a Laboratory Devices Mel-Temp apparatus (Holliston, Mass.).

A. Example 1-2

These examples illustrate comparative preparations of 3-CNT.

1. Preparation of 3-CNT by Cyclization of Cyanoformimidic Acid Hydrazide with Triethylorthoformate Cyanoformimidic acid hydrazide was prepared in 53-62% yield from cyanogen and anhydrous hydrazine followed the procedure described in U.S. Pat. No. 3,004,060.
3-CNT was prepared based on the procedure described in U.S. Pat. No. 3,927,216: In a 250 ml flask fitted with a mechanical stirrer, a temp probe, a cooling bath, and a positive nitrogen set up was placed with cyanoformimidic acid hydrazide 15.0 gm (0.178 mole) and triethyl orthoformate 80.2 gm (0.541 mole). The mixture was chilled to 0-5° C. A 4 gm solution of dioxane which was pre-saturated with HCl gas was added in one portion. The reaction mixture was stirred at 0-5° C. for 5 hours, warmed to ambient temperature, and stirred at ambient temperature until reaction completion (<0.5 area % cyanoformimidic acid hydrazide by HPLC). After reaction completion, excess triethylorthoformate was concentrated under reduced pressure to give crude 3-CNT (12.3 gm, 76 area % pure by HPLC) which was suspended in toluene 248 gm and 202 gm ethyl acetate. The mixture was heated to 75-80° C. and was filtered to remove insolubles. The filtrate was concentrated under reduced pressure to give a slurry. After filtration, the cake washed with toluene 1×10 ml and dried to give a light yellow solid, 10.1 gm (60.2% yield, 98.7 area % HPLC purity).

2. Preparation of 3-CNT by Condensation of 3-chloro-1,2,4-triazole with NaCN

The procedure described in G.B. 1,157,256 was followed: In a 100 ml flask equipped with a mechanical stirrer, a temp probe, a heating mantle, a reflux condenser, and a positive nitrogen set up was placed with 3-chloro-1,2,4-triazole 5.2 gm (50.24 mmoles), NaCN 2.6 gm (53.05 mmoles), and dimethylformamide 55 ml. The mixture was heated to reflux for 16 hours and quenched with 250 ml ice water. The solid was filtered, washed with water, and dried to give a black solid, 0.53 gm (11% yield).

B. Examples 3-5

These examples illustrate the preparation of 3-CNT using the dehydration methods of the present invention.

3. Preparation of 3-CNT by Dehydration with $SOCl_2$

In a 250 ml flask equipped with a mechanical stirrer, a temp probe, a cooling bath and a positive nitrogen set up was placed with 1,2,4-triazloe-3-carboxamide (22.4 gm, 0.20 mole) and acetonitrile 100 ml. The mixture was chilled in an ice water bath. 4-methylmorpholine 56.6 gm (0.56 mole) was added in one portion. Thionyl chloride 47.8 gm (0.40 mole) was added in 2 hours at 5-17° C. Then the mixture was warmed to ambient temperature. Dimethylformamide 3.7 gm (0.051 mole) was added. The mixture was continued to stir at ambient temperature for additional 4 hours. Then the mixture was chilled in an ice water bath before water quench. Water 60 ml was added at 15-34° C. The mixture was extracted with 5×60 ml ethyl acetate. The combined ethyl acetate layer was washed with 2×20 ml 9% NaCl solution and concentrated under reduced pressure to give a yellow solid 13.7 gm (73.0% yield, 96.7 area % purity by HPLC).

TABLE 2

3-CAT Dehydrations:

| Reagent(s) | Solvent(s) | Reaction Temp., ° C./ Reaction Temp., ° C./ Time (h) | Yield, % |
|---|---|---|---|
| $POCl_3$ | MEK | 83/15 | 35.5 |
| $POCl_3$ | | 110/15 | 10.4 |
| $POCl_3$ | AcCN | 83/15 | 85 |
| $SOCl_2$ | | 78/15 | 27.1 |
| $SOCl_2$ | DMF/NMP | | 8.1 |
| $SOCl_2$ | DMF/NMP | | 12.6 |
| $SOCl_2$ | DMF | | 0.0 |
| $SOCl_2$ | DMF/NMP | | 0.0 |
| $SOCl_2$ | DMF/NMP/AcCN | | 56.7 |
| $SOCl_2$ | DMF/NMP/AcCN | | 50 |
| $SOCl_2$ | DMF/NMP | | 54.3 |
| $SOCl_2$ | DMF/NMP | | 73 |
| $SOCl_2$ | DMF/NMP/AcCN | | 68.3 |
| $SOCl_2$ | DMF/NMP/AcCN | | 53.1 |
| $SOCl_2$ | DMF/NMP/AcCN | | 0.0 |
| $SOCl_2$ | DMF/NMP/AcCN | | 48.7 |
| $SOCl_2$ | DMF/NMP/AcCN | | 61.3 |

TABLE 2-continued

3-CAT Dehydrations:

| Reagent(s) | Solvent(s) | Reaction Temp., ° C./ Reaction Temp., ° C./ Time (h) | Yield, % |
|---|---|---|---|
| SOCl$_2$ | DMF/NMP/AcCN | | 50.0 |
| SOCl$_2$ | DMF/NMP/AcCN | | 0.0 |
| SOCl$_2$ | DMF/NMP/AcCN | | 33.4 |
| POCl$_3$ | NMP/AcCN | | 0.0 |
| POCl$_3$ | DMF/NMP/AcCN | | 0.0 |
| TFAA | EtOAc/NMP/TFAA | 5 | 0.0 |
| SOCl$_2$ | DMF/NMP/AcCN | | 0.0 |
| SOCl$_2$ | DMF/NMP/AcCN | | 24.8 |
| SOCl$_2$ | DMF/NMP/AcCN | | 0.0 |
| SOCl$_2$ | Pyridine | 25/1 | 88.0 |
| SOCl$_2$ | Pyridine | 25/2 | 73.0 |
| SOCl$_2$ | Pyridine | 72 | 0.0 |
| SOCl$_2$ | 1,4-Dioxane/Pyridine/TFAA | 25/72 | 91.9 |

4. Preparation of 3-CNT by Dehydration with TFAA

In a 500 ml jacketed flask equipped with a mechanical stirrer, a temp probe, a circulation bath and a positive nitrogen atmosphere set up was placed with 1,2,4-triazole-3-carboxamide 25.3 gm (0.112 mole), 1,4-dioxane 225 gm, and pyridine 72.8 gm (0.92 mole). The mixture was chilled to −6.8° C. Trifluoroacetic anhydride 107.1 gm (0.51 mole) was added dropwise at −1.3 to −6.8° C. in 10 min. Then the mixture was warmed to ambient temperature and stirred for 30 min. Without work up, a sample was taken for HPLC analysis. The chromatogram showed that the product contained 93% 3-CNT and 0.2% 3-CAT.

5. Preparation of 3-CNT by Dehydration with POCl$_3$

In a dried 1-L, three-necked, jacketed flask fitted with a mechanical stirrer, temperature probe, a reflux condenser, a circulation bath, and a positive nitrogen atmosphere set-up was charged with 1,2,4-triazole-3-carboxamide 40.0 gm (0.36 mole), acetonitrile 320 ml, and POCl$_3$ 526.4 gm (3.43 moles). The white slurry mixture was agitated and heated to reflux. The reaction mixture was maintained at reflux for at least 15 hrs. Then the excess POCl$_3$ was distilled off under reduced pressure. After aqueous work up, the reaction mixture was extracted with 4×100 ml ethyl acetate. The combined ethyl acetate extracts were washed with 2×100 ml water, distilled under reduced pressure to remove ethyl acetate and quenched with toluene to form a beige color slurry. After filtration, the cake was washed with 2×30 ml toluene and dried to give 3-cyano-1,2,4-triazole 29.9 g (89.0% yield) as a tan solid: HPLC purity, >99.0 area %; DSC (endotherm peak 186.9° C.).

A large excess of POCl$_3$ can be used but need not be used. The results of molar ratio of POCl$_3$/3-CAT effect on reaction conversion are summarized below.

| 3-CAT (g) | POCl$_3$ (g) | POCl$_3$/3-CAT molar ratio | ACN (mL) | Completion Results (%) |
|---|---|---|---|---|
| 40 | 394.8 | 7.2 | 320 | 98 |
| 40 | 263.3 | 4.8 | 320 | 98.2 |
| 40 | 131.6 | 2.4 | 520 | 99 |
| 40 | 65.8 | 1.2 | 470 | 72 |

Thus, 1,2,4-triazole-3-carboxamide (40.0 g, 0.36 mole) and about 2.4 equivalents of POCl$_3$ (131.6 g, 0.86 mole) in acetonitrile (320 ml-480 ml) also gave high yields of 3-cyano-1,2,4-triazole (27.8 and 29.5 g, 82.8-87.9% yield).

Alternatively, the reaction can be worked-up by distilling off acetonitrile under reduced pressure after the aqueous work up above to give a slurry mixture. After filtration, the cake can be washed with water (2×40 ml) and dried in a vacuum oven at 40-50° C. to give 3-cyano-1,2,4-triazole (28.4 g, 84.6% yield).

C. Example 6

These examples illustrate the preparation of 4-cyanoimidazole using the dehydration methods of the present invention.

6. Preparation of 4-Cyanoimidazole

In a dried 125 mL, three-neck flask fitted with a magnetic stirrer, temperature probe, a reflux condenser, and a positive nitrogen atmosphere set-up was charged with 4-imidazole carboxamide 2.0 gm (18 mmol), acetonitrile 25 ml, and POCl$_3$ 6.6 gm (43.2 mmol). The brown slurry was agitated and heated to reflux. The reaction mixture was maintained at reflux for at least 15 hrs. Then the excess POCl3 was distilled under reduced pressure. After aqueous work up, the reaction mixture was adjusted to a pH of 9-11 using 25% sodium hydroxide, and extracted with 4×70 ml ethyl acetate. The combine ethyl acetate extracts were treated with 20 gm silica gel, distilled under pressure to remove ethyl acetate and to afford 4-cyanoimidazole as a white solid. After drying the 4-cyanoimidazole weighed 1.1 gm (65.9% yield): HPLC purity, >99.0 area %; $^1$H NMR (300 MHz, DMSO-D6) δ 7.89 (s, 1H), 8.08 (s, 1H); $^{13}$C NMR (300 MHz, DMSO-D6) δ 111.8, 116.0, 127, 138.1.

D. Example 7

These examples illustrate the preparation of 3-CNT using the dehydration methods of the present invention.

7. Preparation of 2-Cyanopyrazine

In a dried 500 ml, three necked, jacketed flask fitted with a mechanical stirrer, temperature probe, a reflux condenser, a circulation bath, and a positive nitrogen atmosphere set-up was charged with 2-pyrazinecarboxamide 20.0 gm (0.162 mol), acetonitrile 240 ml, and POCl$_3$ 59.6 gm (0.389 mol). The white slurry was agitated and heated to reflux. The reaction mixture was maintained at reflux for at least 6 hours. Then the excess POCl$_3$ was distilled off under reduced pressure. After aqueous work up, the reaction mixture was extracted with 4×70 ml ethyl acetate. The combine ethyl acetate extracts were washed with 3×70 ml water, distilled under reduced pressure to remove ethyl acetate and to afford cyanopyrazine as a brown oil: 5.76 gm (34% yield); HPLC purity, >98 area %; $^1$H NMR (300 MHz, CDCl$_3$) δ 8.67 (pair d, J=1.7 and 2.5 1H), 8.75 (d, J=2.5, 1H), 8.87 (d, J=1.3 1H); $^{13}$C NMR (300 MHz, CDCl$_3$) δ 115.1, 130.7, 145.3, 147.3, 148.1.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. The examples given above are non-limiting in that one of ordinary skill in view of the above will readily envision other permutations and variations on the invention without departing from the principal concepts. Such permutations and variations are also within the scope of the present invention. All the patents, journal articles and other documents discussed or cited above are herein incorporated by reference. The invention is further illustrated with reference to the claims that follow thereto.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A method for preparing a compound of Formula (I):

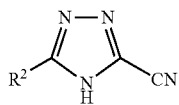

(I)

or a tautomer or salt thereof; said method comprising dehydrating a compound of Formula (II):

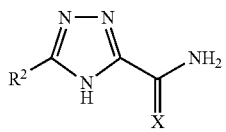

(II)

with at least one dehydrating agent selected from the group consisting of trifluoroacetic anhydride, thionyl chloride, and phosphorus oxychloride in at least one solvent selected from the group consisting of acetonitrile, 1,4-dioxane, ethyl acetate, 1-methyl-2-pyrrolidinone, and pyridine; to form a compound of formula (I);
wherein:
X is O or S; and
$R^2$ is-selected from the group consisting of $C_{1-8}$alkyl, aryl and halogen.

2. The method of claim 1, wherein X is S.

3. The method of claim 1, wherein X is O.

4. The method of claim 1, wherein said dehydrating agent is present in an amount ranging from 2.5 equivalents to 9 equivalents to the amount of the compound of Formula (II).

5. The method of claim 1, wherein said dehydrating agent is present at a concentration ranging from 3 molar equivalents to 28 molar equivalents to the amount of the compound of Formula (II).

6. The method of claim 1, wherein said method further comprises carrying out the dehydration at a temperature ranging from 0° C. to 160° C.

7. The method of claim 1, wherein said method further comprises quenching the reaction with a quenching agent selected from the group consisting of water, $NaHCO_3$, $Na_2CO_3$, NaOH, KOH, $NH_4OH$, and triethylamine.

8. The method of claim 1, wherein said dehydrating agent is $POCl_3$.

9. The method of claim 1, wherein the solvent is acetonitrile.

10. The method of claim 1, wherein the compound of Formula (I) has the structure:

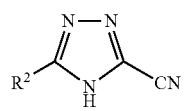

(Iai)

wherein $R^2$ is selected from the group consisting of H, $C_{1-8}$alkyl, aryl and halogen; or a tautomer or salt thereof; said method comprising dehydrating a compound of Formula (IIai):

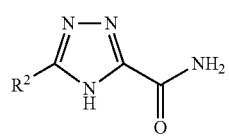

(IIai)

by contacting the compound of Formula (IIai) with phosphorus oxychloride in acetonitrile.

11. The method of claim 1, further comprising producing a salt of the compound of Formula (I).

12. The method of claim 1, further comprising isolating the compound of Formula (I).

13. The method of claim 1, wherein said method further comprises an organic base soluble in said reaction mixture.

14. The method of claim 13, wherein said organic base is pyridine.

15. The method of claim 1, wherein said method further comprises purifying said compound of Formula (I) by extraction or filtration.

16. The method of claim 15, wherein said extraction comprises contacting the compound of Formula (I) with a solvent mixture selected from the group consisting of water/ethyl acetate, water/isopropyl acetate and water/2-methyltetrahydrofuran.

17. The method of claim 15, wherein said filtration comprises contacting the compound of Formula (I) with a solvent in which the compound of Formula (I) is insoluble and filtering the mixture to provide purified compound of Formula (I).

18. The method of claim 17, wherein the solvent in which the compound of Formula (I) is insoluble is toluene.

19. A method for preparing a compound of Formula (I):

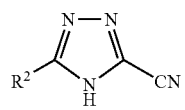

(I)

or a tautomer or salt thereof; said method comprising dehydrating a compound of Formula (II):

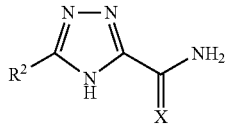
(II)

with at least one dehydrating agent selected from the group consisting of trifluoroacetic anhydride, and thionyl chloride, in at least one solvent selected from the group consisting of acetonitrile, 1,4-dioxane, ethyl acetate, 1-methyl-2-pyrrolidinone, and pyridine; to form a compound of formula (I); wherein:
X is O or S; and
R² is selected from the group consisting of H, C₁₋₈alkyl, aryl and halogen.

20. A method for preparing a compound of Formula (I):

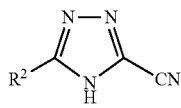
(I)

or a tautomer or salt thereof; said method comprising dehydrating a compound of Formula (II):

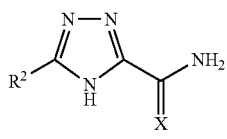
(II)

with at least one dehydrating agent selected from the group consisting of trifluoroacetic anhydride, thionyl chloride, and phosphorus oxychloride in at least one solvent selected from the group consisting of 1,4-dioxane, ethyl acetate, 1-methyl-2-pyrrolidinone, and pyridine; to form a compound of formula (I);
wherein:
X is O or S; and
R² is selected from the group consisting of C₁₋₈alkyl, aryl and halogen.

21. A method for preparing a compound of Formula (I):

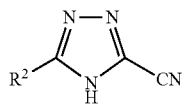
(I)

or a tautomer or salt thereof; said method comprising dehydrating a compound of Formula (II):

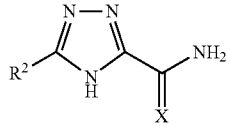
(II)

with at least one dehydrating agent selected from the group consisting of trifluoroacetic anhydride, thionyl chloride, and phosphorus oxychloride in at least one solvent selected from the group consisting of acetonitrile, 1,4-dioxane, ethyl acetate, 1-methyl-2-pyrrolidinone, and pyridine; to form a compound of formula (I);
wherein:
X is S; and
R² is-selected from the group consisting of H, C₁₋₈alkyl, aryl and halogen.

* * * * *